(12) United States Patent
Ryu et al.

(10) Patent No.: US 11,145,049 B2
(45) Date of Patent: Oct. 12, 2021

(54) METHOD FOR ANALYZING POLYMER MEMBRANE

(71) Applicant: LG Chem, Ltd., Seoul (KR)

(72) Inventors: Hyung Ju Ryu, Daejeon (KR); Se Jin Ku, Daejeon (KR); Mi Sook Lee, Daejeon (KR); Sung Soo Yoon, Daejeon (KR)

(73) Assignee: LG Chem, Ltd.

( * ) Notice: Subject to any disclaimer, the term of this patent is extended or adjusted under 35 U.S.C. 154(b) by 108 days.

(21) Appl. No.: 16/629,858

(22) PCT Filed: Jul. 16, 2018

(86) PCT No.: PCT/KR2018/008019
§ 371 (c)(1),
(2) Date: Jan. 9, 2020

(87) PCT Pub. No.: WO2019/013603
PCT Pub. Date: Jan. 17, 2019

(65) Prior Publication Data
US 2020/0402224 A1    Dec. 24, 2020

(30) Foreign Application Priority Data

Jul. 14, 2017   (KR) .................. 10-2017-0089864

(51) Int. Cl.
*G06T 7/00*       (2017.01)
*G01N 23/04*    (2018.01)
*G01N 33/44*    (2006.01)
*G01Q 30/06*    (2010.01)
*G06T 5/00*       (2006.01)
*G06T 5/10*       (2006.01)

(52) U.S. Cl.
CPC ........... *G06T 7/0006* (2013.01); *G01N 23/04* (2013.01); *G01N 33/44* (2013.01); *G01Q 30/06* (2013.01); *G06T 5/002* (2013.01); *G06T 5/10* (2013.01); *G06T 2207/10061* (2013.01)

(58) Field of Classification Search
CPC   G06T 7/006; G06T 5/002; G06T 5/10; G06T 2207/10061; G01N 23/04; G01N 33/44; G01Q 30/06
USPC ......................................................... 382/141
See application file for complete search history.

(56) References Cited

U.S. PATENT DOCUMENTS

2002/0118864 A1   8/2002   Kondo et al.
2004/0262529 A1   12/2004   Yoshida et al.
(Continued)

FOREIGN PATENT DOCUMENTS

JP   2002259981 A   9/2002
JP   2004233163 A   8/2004
(Continued)

OTHER PUBLICATIONS

Extended European Search Report including Written Opinion for Application No. EP18832906.4, dated Jun. 8, 2020, pp. 1-7.
(Continued)

*Primary Examiner* — Mark Roz
(74) *Attorney, Agent, or Firm* — Lerner, David, Littenberg, Krumholz & Mentlik, LLP

(57) ABSTRACT

A method for analyzing a polymer membrane, which can improve accuracy of structural analysis of the polymer membrane and shorten the analysis time by effectively removing noise is provided.

5 Claims, 8 Drawing Sheets

(56) References Cited

U.S. PATENT DOCUMENTS

| | | | |
|---|---|---|---|
| 2007/0172150 A1 | 7/2007 | Quan et al. | |
| 2008/0013821 A1* | 1/2008 | Macgregor | G05B 19/41875 |
| | | | 382/141 |
| 2011/0284759 A1 | 11/2011 | Kono et al. | |
| 2015/0228063 A1 | 8/2015 | Minakawa et al. | |
| 2016/0280832 A1 | 9/2016 | Kim et al. | |
| 2017/0140522 A1 | 5/2017 | Nam et al. | |

FOREIGN PATENT DOCUMENTS

| | | | |
|---|---|---|---|
| JP | 2006106243 A | 4/2006 | |
| JP | 3837543 B2 | 10/2006 | |
| JP | 2012182806 A | 9/2012 | |
| JP | 5178558 B2 | 4/2013 | |
| JP | 2013200298 A | 10/2013 | |
| JP | 201481220 A | 5/2014 | |
| JP | 2016540082 A | 12/2016 | |
| KR | 100784599 B1 | 12/2007 | |
| KR | 20090073470 A | 7/2009 | |
| KR | 20170055709 A | 5/2017 | |
| WO | 2008039551 A1 | 4/2008 | |

OTHER PUBLICATIONS

Welander et al., Impact of trench width roughness on the graphoepitaxial assembly of block copolymers, Journal of Vacuum Science and Technology B., Dec. 2008, pp. 2484-2488, vol. 26. No. 6, XP012114498.
Search report from International Application No. PCT/KR2018/008019, dated Nov. 5, 2018.
Lee, Junyoung et al., "Microstructures of Triblock Copolymers" Polymer Science and Technology, vol. 23, No. 5, Oct. 31, 2012, pp. 525-540. (English translation of Abstract only).

* cited by examiner

[Figure 1]
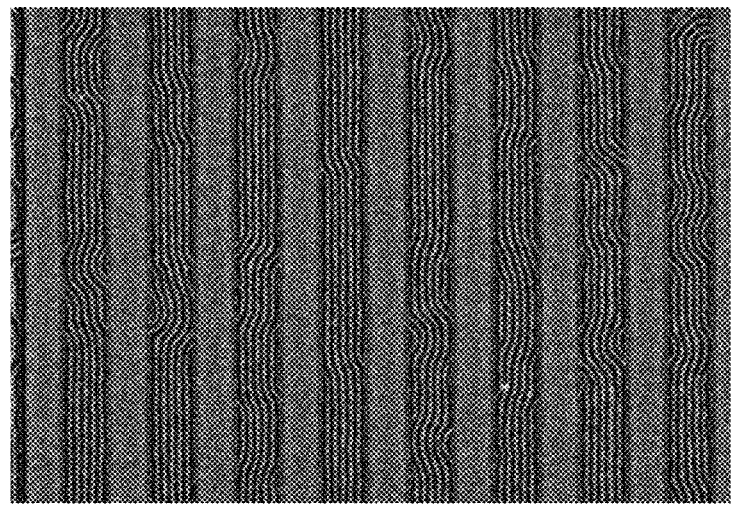
[Figure 2]
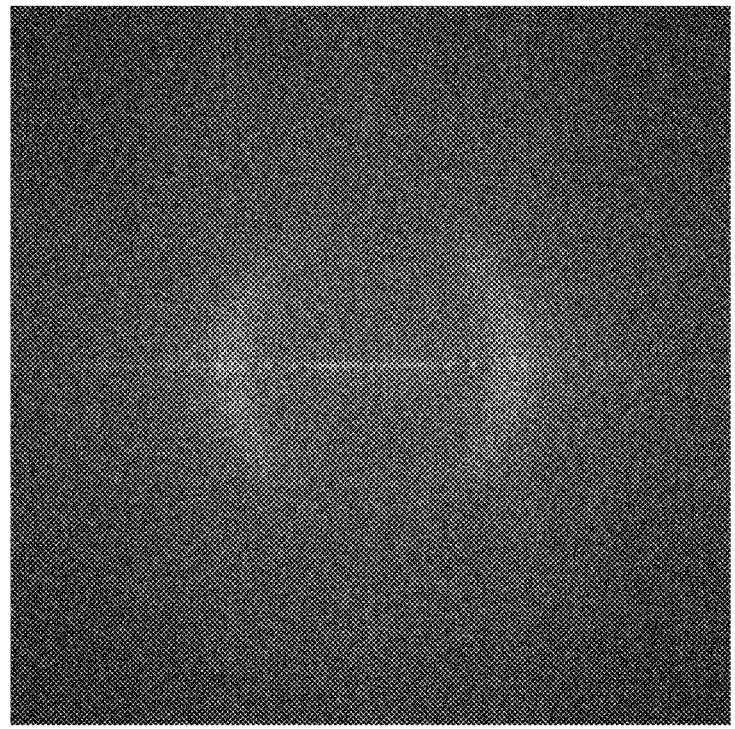

[Figure 3]
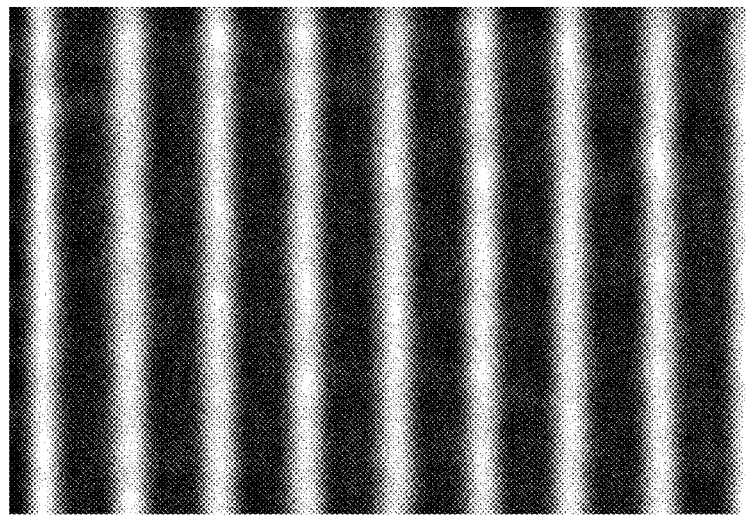
[Figure 4]
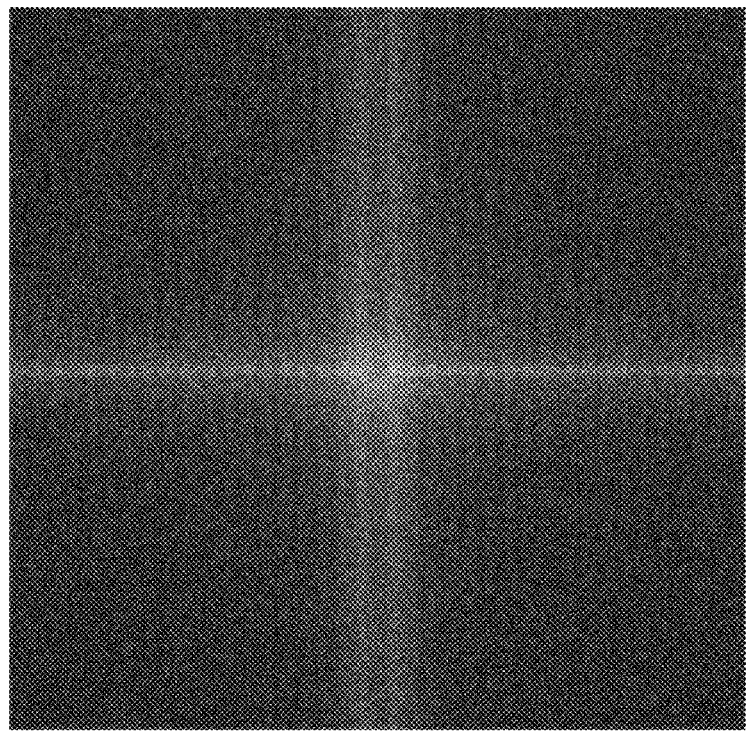

[Figure 5]
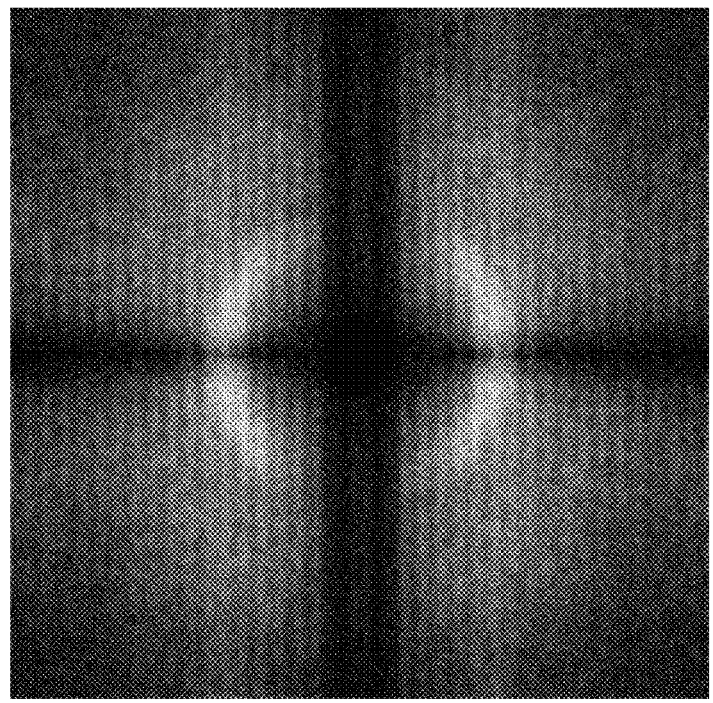
[Figure 6]
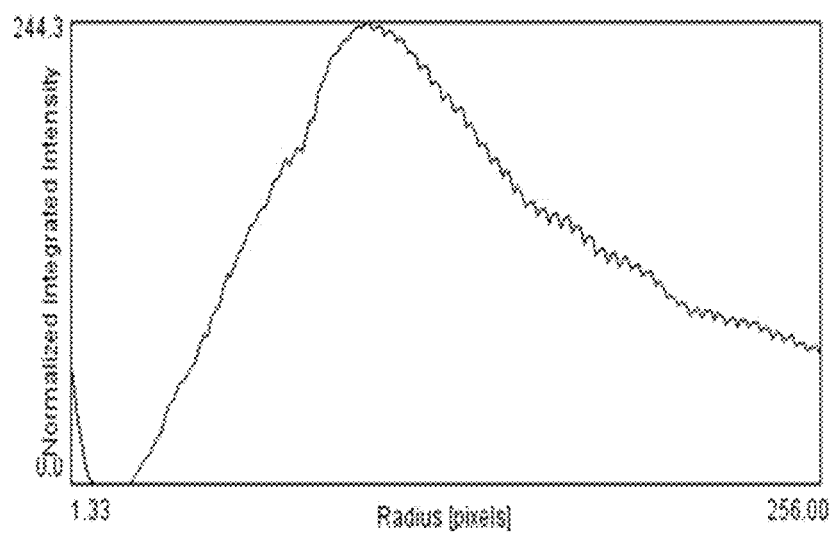

[Figure 7]
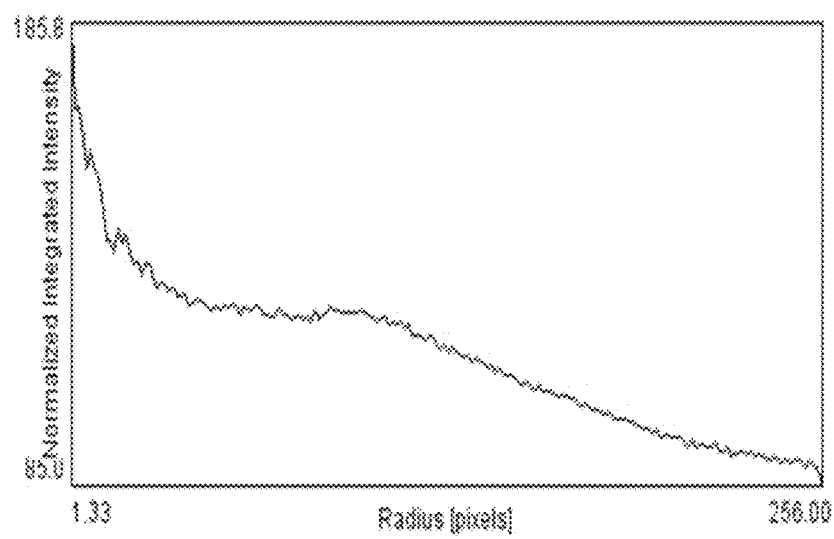
[Figure 8]
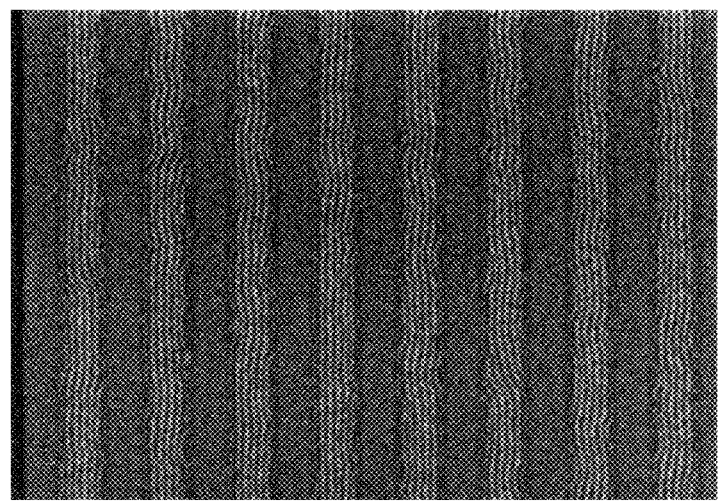

[Figure 9]
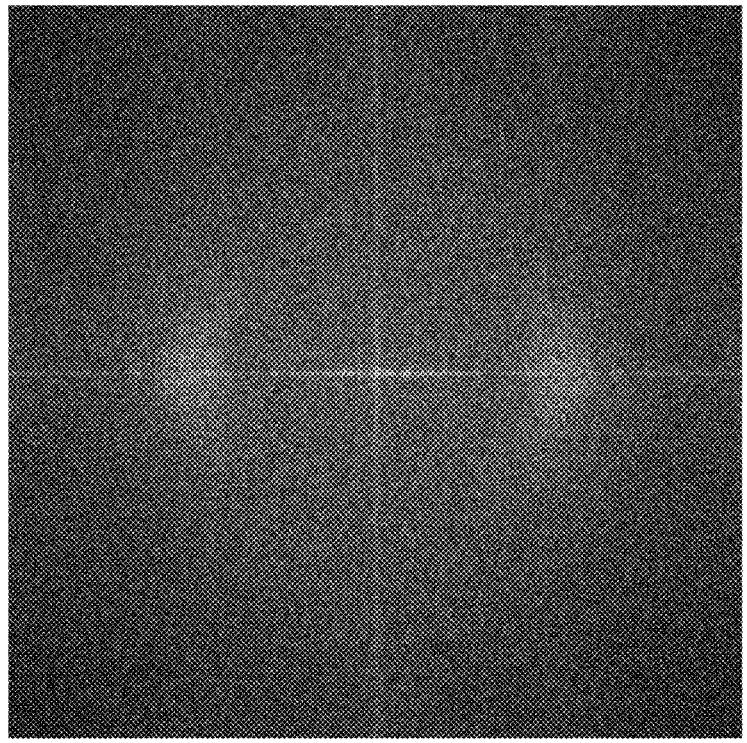
[Figure 10]
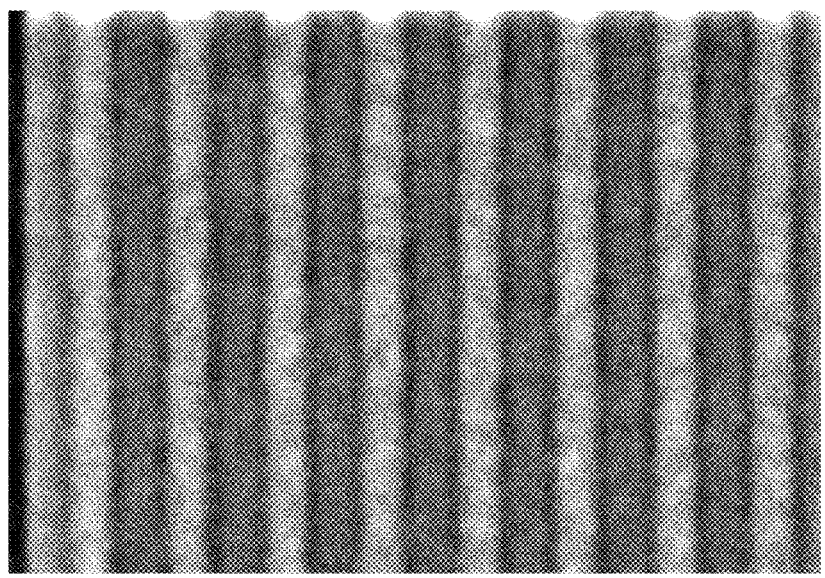

[Figure 11]
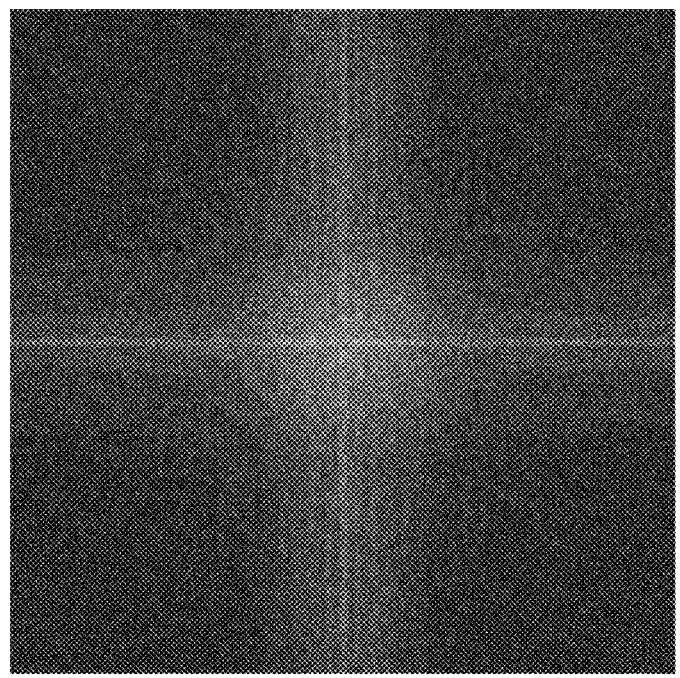

[Figure 12]
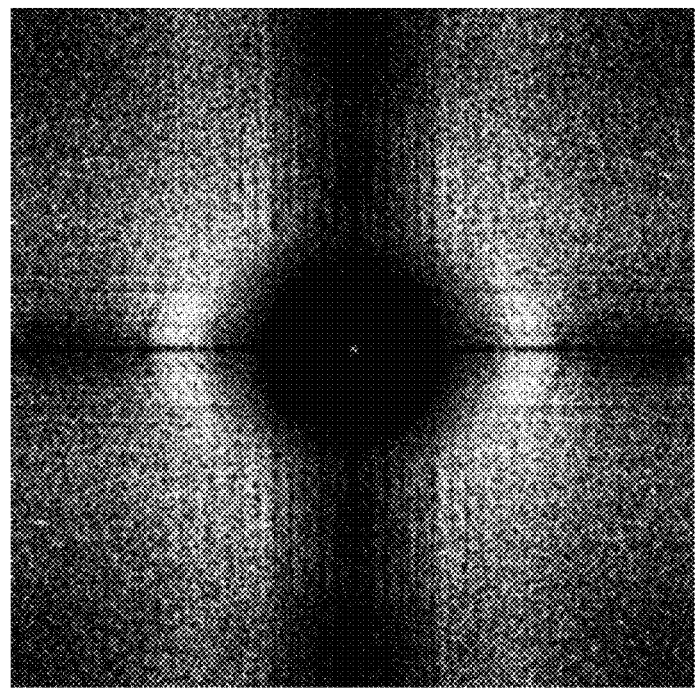
[Figure 13]
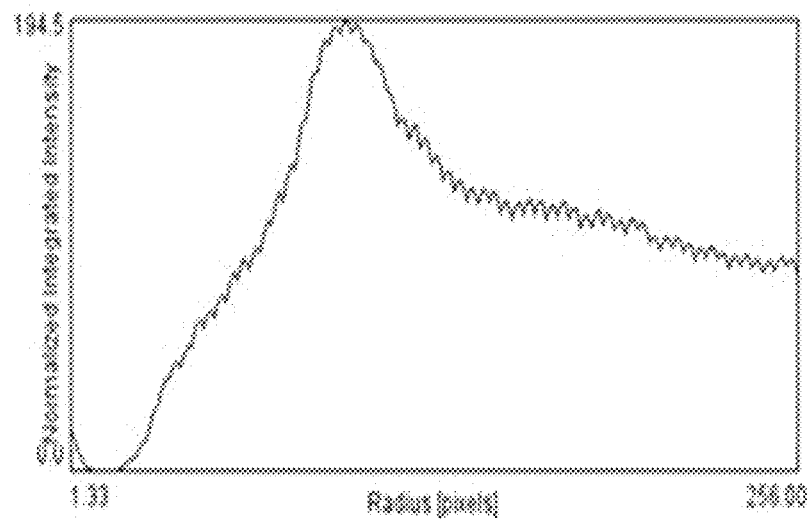

[Figure 14]
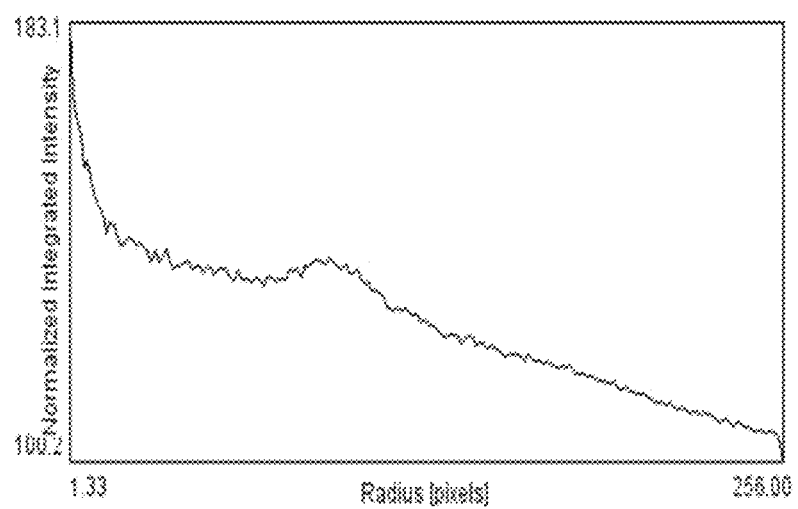

METHOD FOR ANALYZING POLYMER MEMBRANE

CROSS-REFERENCE TO RELATED APPLICATIONS

The present application is a national phase entry under 35 U.S.C. § 371 of International Application No. PCT/KR2018/008019 filed on Jul. 16, 2018, which claims priority from Korean Patent Application No. 10-2017-0089864 filed on Jul. 14, 2017, the disclosure of which is incorporated herein by reference in its entirety.

TECHNICAL FIELD

The present application relates to a method for analyzing a polymer membrane.

BACKGROUND ART

Block copolymers in which two or more chemically distinct polymer chains are linked by covalent bonds can be separated into regular microphases due to their self assembly characteristics. The microphase separation phenomenon of such a block copolymer is generally explained by volume fractions, molecular weights and mutual attraction coefficients (Flory-Huggins interaction parameter) between constituents, and it may form various structures with nano-scale spheres, cylinders, gyroids or lamellae, and the like.

An important issue in practical applications of various nanostructures formed by the block copolymers is to control orientation of microphases of the block copolymer. If the spherical block copolymer nanostructure is a zero-dimensional structure having no direction of special orientation, the cylindrical or lamellar nanostructure has orientation as one-dimensional and two-dimensional structures, respectively. Typical orientation properties of the block copolymer may include a parallel orientation in which the orientation of the nanostructure is parallel to the substrate direction and a vertical orientation in which the orientation of the nanostructure is vertical to the substrate direction, where the vertical orientation often has greater importance than the parallel orientation.

Typically, the orientation of the nanostructure in the membrane of the block copolymer can be determined by whether any one of the blocks of the block copolymer is exposed to the surface or air. That is, the orientation of the nanostructure can be determined by selective wetting of the relevant block, where since a plurality of substrates is generally polar and air is non-polar, a block having a larger polarity in a block copolymer is wetted on a substrate and a block with a smaller polarity is wetted at the interface with air, whereby the parallel orientation is induced.

DISCLOSURE

Technical Problem

In order to utilize a self-assembled structure of a block copolymer efficiently, it should be possible to first accurately analyze the structure formed by the block copolymer. However, when the structure of the block copolymer is analyzed by imaging, errors due to noise or the like may occur. Particularly, when the block copolymer is aligned in trenches using graphoepitaxy, the line structures of the trenches and the block copolymer are aligned in the same direction, so that there is a problem that many errors occur in the image analysis of the block copolymer structure.

Technical Solution

In this specification, the term "image" may mean visual information recognizable by human vision, which is reproduced and displayed on a two-dimensional or three-dimensional screen, and may mean various visual information such as still images and videos. The still image or video may be one obtained by using an optical sensor, such as a charge-coupled device (CCD), which is a semiconductor element and digitally acquiring an image coming from a subject to the sensor, and may comprise an image or the like obtained by visually transforming the result value measured using an electron microscope or other measurement equipment. In addition, the "original image" may mean an image itself obtained from the sensor or the like, and may mean an image in which no separate post-processing is performed.

In this specification, the "Fourier transformation" means to transform pixel values of an image into values in a frequency domain. The Fourier transformation is a widely used technique in signal processing, which is based on the concept that one signal can be represented by synthesis of several sinusoidal signals and can analyze low frequency and high frequency components existing in the image.

In this specification, the "transformation" may mean changing a format of data according to the designated algorithm. The transformation may mean changing the position, size or property by moving any subject to another position, enlarging, reducing or rotating it, or by expressing it by changing it from one coordinate system to another coordinate system, which may be, for example, a concept including Fourier transformation, image blurring, and the like.

The image, transformation, Fourier transformation, and the like can be performed using a known numerical analysis program or image processing program, and the like, and the post-processing can be performed to the image using, for example, an image analysis software (US National Institute of Health [NIH] open source, "Image J" or MathWorks, Inc., "MATLAB"), and the like.

The present application relates to a method for analyzing a polymer membrane. The analysis method of the present application may comprise a step of blurring an original image of a polymer membrane having a block copolymer which is formed in trenches disposed at regular intervals and self-assembled. The method of obtaining the image of the polymer membrane is not particularly limited, where the image of the polymer membrane may be digitally acquired using an optical sensor, or may be acquired by visually transforming the result value measured using an electron microscope or other measurement equipment, and the image may be obtained, for example, through a scanning electron microscope (SEM), an atomic force microscope (AFM), or a transmission electron microscope (TEM).

The method of blurring the obtained image is not particularly limited, which can be performed by a known method. The blurring processing may mean a method of blurring the part which is an outline of the digital image by removing high frequency components (those having a large change rate of pixel values) of the digital image or removing extreme values from the pixel values and assigning the result value that is averaged with neighboring pixels. The blurring processing can use various known blur methods without limitation as long as it can give a blur effect to an image, and for example, a method such as low pass filtering, Gaussian blur, motion blur or radial blur can be used. By performing the blurring processing on the image of the polymer membrane to separate the region corresponding to the trenches and the region corresponding to the self-assembled block copolymer from the original image of the polymer membrane, accurate analysis of the image of the polymer membrane can be allowed. As the method of blurring an image, a known image processing program or the like can be used, and for example, the Fourier transformation can be performed on the obtained image using an image analysis software (US National Institute of Health [NIH] open source, "Image J" or MathWorks, Inc., "MATLAB"), and the like.

In one example of the present application, it may further comprise a step of Fourier-transforming the obtained original image and the blurred image. The method of performing the Fourier transformation on the obtained original image and the blurred image is not particularly limited, which can be performed by a known method. As the method of Fourier-transforming an image, a known image processing program or the like can be used, and for example, the Fourier transformation can be performed on the obtained image using an image analysis software (US National Institute of Health [NIH] open source, "Image J" or MathWorks, Inc., "MATLAB"), and the like.

When the Fourier transformation is performed on the obtained image, the Fourier-transformed image can be obtained. The Fourier-transformed image shows the result that the pixel values of the image are transformed into frequency domain values. Generally, the low frequency region of the Fourier-transformed image represents information on the overall brightness of the image, and the high frequency region represents information on the edge or noise of the image. Through the Fourier transformation, only the information about the noise components included in the image of the polymer membrane can be separated and removed, thereby reducing errors upon analyzing the polymer membrane. By Fourier-transforming the blurred image, it is possible to clarify the difference between the part where the polymer membrane is formed on the substrate and the part where the polymer membrane is not formed thereon, whereby in the analysis of the polymer membrane, the analysis only on the part where the polymer membrane is formed can be allowed.

In one example, the method for analyzing a polymer membrane according to the present application may further comprise a step of removing noise from the image generated by the Fourier transformation. Noise can be removed from the Fourier-transformed image, thereby reducing errors upon analyzing the polymer membrane. The step of removing noise may be a step of removing the overlapping range of the Fourier transformation result of the original image and the Fourier transformation result of the blurred image. By removing the range overlapped with the result of Fourier-transforming the image subjected to the Fourier-transformation after blurring processing from the result of Fourier-transforming the original image, only the region corresponding to the noise other than the polymer membrane can be removed and only the region on the information of the polymer membrane can be acquired. The method of removing the range overlapped with the result of Fourier-transforming the image subjected to the Fourier-transformation after blurring processing from the result of Fourier-transforming the original image is not particularly limited, which can be performed, for example, using a known image analysis software or the like.

The method for analyzing a polymer membrane of the present application may comprise a step of measuring the pitch of the pattern formed on the surface of the polymer membrane from the Fourier-transformed result of the noise-removed original image. The pattern may mean a shape formed due to a self-assembled structure of a block copolymer to be described below, and may mean a pattern including two or more lines. By measuring the pitch of the pattern from the Fourier-transformed image, it is possible to accurately analyze the self-assembled structure of the polymer membrane.

In one example of the present application, the pitch of the pattern formed on the surface of the polymer membrane can be measured by converting a two-dimensional spectral image formed by Fourier transformation into a one-dimensional graph through radial integration. Specifically, the step of measuring a pitch is a step of measuring a peak formed by radially integrating the Fourier-transformed image of the polymer membrane in the range of 0° to 360°. If the Fourier-transformed two-dimensional image is radially integrated in the range of 0° to 360°, the one-dimensional graph expressing the density of frequency can be obtained, where the X coordinate value of the first peak on the frequency domain graph may mean the pitch of the actual region of the pattern formed on the surface of the polymer membrane. By measuring the pitch of the pattern formed on the surface of the polymer membrane using the peak value, it is possible to accurately analyze the structure of the polymer membrane.

The polymer membrane of the present application may be formed on a substrate on which trenches are formed. The type of the substrate applied to the method of the present application is not particularly limited. As the substrate, for example, various types of substrates requiring formation of a pattern on the surface may all be used for applying each of the above-described applications. A substrate of this type may include a semiconductor substrate such as a silicon substrate, a silicon germanium substrate, a GaAs substrate and a silicon oxide substrate. As the substrate, for example, a substrate may be used, which is applied to form finFETs (fin field effect transistors) or other electronic devices such as diodes, transistors or capacitors. In addition, other materials such as ceramics may be used as the substrate depending on applications, and the types of substrates that can be applied in the present application are not limited thereto.

Mesa structures may be formed on the surface of the substrate applied to the method of the present application from each other at intervals, and trenches may be formed by the mesa structures. For example, the mesa structures may each be in the form of a line. Such mesa structures may be spaced apart from each other at regular intervals and disposed on the substrate surface. The mesa structures may be disposed substantially parallel to one another on the surface of the substrate. At least two or more mesa structures may be formed on the surface of the substrate. That is, the number of trenches formed by the mesa structures on the surface of the substrate may be one or more. The number of the mesa structures and the trenches is not particularly limited, which may be adjusted depending on applications.

The ratio (D/H) of the distance (D) of the mesa structures spaced apart to form the trench to the height (H) of the mesa structure is not particularly limited, which may be, for example, 0.1 or more and may be 10 or less. In addition, the ratio (D/W) of the distance (D) between the mesa structures to the width (W) of the mesa structure is not particularly limited, which may be 0.5 or more and may be 10 or less. The ratio (D/H or D/W) may be changed according to the intended use. In this specification, the term distance (D) of mesa structures means the shortest distance between adjacent mesa structures spaced apart, where the distance (D) may be, for example, 5 nm or more and may be 500 nm or less. In this specification, the term height (H) of mesa structure is a dimension of a mesa structure measured in the upward direction along the normal direction of the substrate surface based on the surface of the substrate, which may be, for example, 1 nm or more and may be 100 nm or less. In this specification, the term width (W) of mesa structure is a dimension of a mesa structure measured along the direction vertical to the normal direction of the substrate surface, which may be, for example, 5 nm or more and may be 500 nm or less. For example, when the block copolymer is applied as the inductive self-assembly material and the lamella pattern of the block copolymer is formed, the distance of mesa structures may be in a range of about 1 L to 20 L. In this case, the membrane comprising the block copolymer, i.e. the membrane formed in the trenches, may have a thickness in the range of about 0.1 L to 10 L or 1 L to 8 L. The dimension or the like of the mesa structure is one example of the present application, which can be changed according to a specific aspect.

A method of forming such mesa structures on a substrate is not particularly limited, where a known method can be applied. For example, the mesa structures can be formed by etching the substrate in an appropriate manner, or by depositing an appropriate material on the substrate.

Here, the kind of the mesa structure forming material is not particularly limited. For example, as the material, a material capable of being etched by an etching process to form a mesa structure may be used. For example, as the material, SiO2, ACL (amorphous carbon layer), SOG (spin-on-glass), SOC (spin-on-carbon) or silicon nitride, and the like may be applied. The layer of such a material may be coated by a method such as spin coating or may be formed by a vapor deposition method such as CVD (chemical vapor deposition). When the layer of the material is formed, its thickness or the like is not particularly limited, and the layer may be formed to have an appropriate thickness in consideration of the height (H) of the desired mesa structure.

In one example of the present application, the polymer membrane may comprise a block copolymer. The block copolymer may be a block copolymer having a first block and a second block chemically distinct from the first block. The block copolymer may mean a molecular structure in which polymer blocks having different chemical structures are linked through covalent bonds.

The block copolymer may form a self-assembled structure. The self-assembled structure may mean that a specific structure is formed by interaction between the respective blocks included in the block copolymer. The self-assembled structure of the block copolymer may be a sphere, cylinder or lamella structure. In one example, the block copolymer may be present in a vertically oriented state in the case of the sphere or lamellar of the structures. For example, within the segments of the first or second block or other blocks covalently bonded thereto in the block copolymer, the other segments may be vertically oriented, while forming a regular structure such as a lamellar shape or a cylinder shape. The block copolymer that can be included in the polymer membrane of the present application is not particularly limited.

The block copolymer of the present application may be a diblock copolymer comprising the first block and the second block as described above, or may be a multi-block copolymer that comprises one or more of the first block and the second block by two or more, or comprises a different type of third block.

The method of forming such a polymer membrane using a block copolymer is not particularly limited. For example, the method of forming a polymer membrane may comprise a process of forming a layer of the block copolymer or a coating solution obtained by diluting it in an appropriate solvent on a neutral layer by coating or the like, and if necessary, aging or heat-treating the layer.

The aging or heat treatment may be performed based on, for example, the phase transition temperature or the glass transition temperature of the block copolymer, and may be performed at, for example, a temperature above the glass transition temperature or the phase transition temperature. The time for which this heat treatment is performed is not particularly limited, and it can be performed in a range of, for example, about 1 minute to 72 hours, but this can be changed as required. In addition, the heat treatment temperature of the polymer thin membrane may be, for example, 100° C. to 250° C. or so, but this may be changed in consideration of the block copolymer to be used. In another example, the formed layer may also be solvent-aged for about 1 minute to 72 hours in a non-polar solvent and/or a polar solvent at room temperature.

Advantageous Effects

The method for analyzing a polymer membrane of the present application can improve accuracy of structural analysis of the polymer membrane and shorten the analysis time by effectively removing noise.

BRIEF DESCRIPTION OF DRAWINGS

FIG. 1 is an SEM photograph of a polymer membrane including a block copolymer formed in trenches.

FIG. 2 is an image Fourier-transforming the image of FIG. 1.

FIG. 3 is an image obtained by performing blurring processing on the image of FIG. 1.

FIG. 4 is an image Fourier-transforming the image of FIG. 3.

FIG. 5 is an image removing the region overlapping with FIG. 4 from FIG. 2.

FIG. 6 is the result of integrating the image of FIG. 5.

FIG. 7 is the result of integrating the image of FIG. 2.

FIG. 8 is a SEM photograph of a polymer membrane including a block copolymer formed in trenches.

FIG. 9 is an image Fourier-transforming the image of FIG. 8.

FIG. 10 is an image obtained by performing blurring processing on the image of FIG. 8.

FIG. 11 is an image Fourier-transforming the image of FIG. 10.

FIG. 12 is an image removing the region overlapping with FIG. 11 from FIG. 9.

FIG. 13 is the result of integrating the image of FIG. 12.

FIG. 14 is the result of integrating the image of FIG. 9.

MODE FOR INVENTION

Hereinafter, the present application will be described more in detail by way of examples according to the present application and comparative examples, but the scope of the present application is not limited by the following examples.

Example 1

A trench substrate was prepared in the following manner. A silicon wafer was applied as a substrate. A layer of SiO was formed on the substrate to a thickness of about 200 nm or so by a known deposition method. Subsequently, a BARC (bottom anti-reflective coating) was coated on the layer of SiO to a thickness of about 60 nm or so, and a PR (photoresist, for KrF, positive-tone resist) layer was again coated thereon to a thickness of about 400 nm or so. Subsequently, the PR layer was patterned by a KrF stepper exposure method. Subsequently, using the patterned PR layer as a mask, the lower BARC layer and SiO layer were etched by an RIE (reactive ion etching) method, and the residue was removed to form a trench structure.

A random copolymer of a compound (DPM-C12) and pentafluorostyrene was coated inside the trenches and fixed on the silicon wafer through a thermal annealing process at 160° C. for 24 hours, and to remove unreacted materials, a sonication process was treated on a fluorobenzene solution for 10 minutes. A coating solution prepared by diluting a block copolymer of a compound (DPM-C12) of Formula A below and pentafluorostyrene in toluene in a solid content concentration of 1.5 wt % was spin-coated inside the trenches, dried at room temperature for about 1 hour and then again subjected to the thermal annealing at a temperature of about 160 to 250° C. for about 1 hour to form a self-assembled membrane.

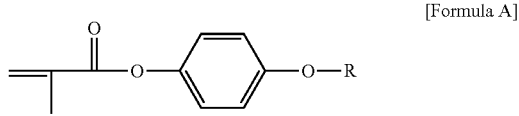

[Formula A]

In Formula A, R is a linear alkyl group having 12 carbon atoms.

FIG. 1 is a SEM photograph of a polymer membrane formed in the above manner. The image of FIG. 1 was Fourier-transformed using image analysis software (US National Institute of Health [NIH] open source, "Image J"). FIG. 2 is the Fourier-transformed image of the polymer membrane.

Furthermore, FIG. 3 is an image obtained by blurring the image of FIG. 1 using image analysis software (US National Institute of Health [NIH] open source, "Image J"), and FIG. 4 is an image Fourier-transforming the blurring-processed FIG. 3 using the same program.

The region overlapping with FIG. 4 was removed from the image of FIG. 2, where FIG. 5 is the image of FIG. 2 after removing the region overlapping with FIG. 4.

The image of FIG. 5 was subjected to radial integration in the range of 0° to 360° using image analysis software (US National Institute of Health [NIH] open source, "Image J"). FIG. 6 shows the integration result, where as a result of measuring the X coordinate of the first main peak formed in the frequency region of FIG. 6 with Image J, the actual region pitch 26.4 nm was measured. This means the pitch of the vertically oriented lamellar structure formed by the self-assembled structure of the polymer membrane formed inside the trench.

Example 2

A coating solution prepared by diluting a block copolymer of a compound (DPMC12) and pentafluorostyrene in toluene in a solid content concentration of 1.5 wt % was spin-coated inside the trenches manufactured by the method mentioned in Example 1, dried at room temperature for about 1 hour and then again subjected to the thermal annealing at a temperature of about 160 to 250° C. for about 1 hour to form a self-assembled membrane.

FIG. 8 is a SEM photograph of a polymer membrane formed in the above manner. The image of FIG. 8 was Fourier-transformed using image analysis software (US National Institute of Health [NIH] open source, "Image J"). FIG. 9 is the Fourier-transformed image of the polymer membrane.

Furthermore, FIG. 10 is an image obtained by blurring the image of FIG. 8 using image analysis software (US National Institute of Health [NIH] open source, "Image J"), and FIG. 11 is an image Fourier-transforming the blurring-processed FIG. 10 using the same program.

The region overlapping with FIG. 11 was removed from the image of FIG. 9, where FIG. 12 is the image of FIG. 9 after removing the region overlapping with FIG. 11.

The image of FIG. 12 was subjected to radial integration in the range of 0° to 360° using image analysis software (US National Institute of Health [NIH] open source, "Image J"). FIG. 13 shows the integration result, where as a result of measuring the X coordinate of the first main peak formed in the frequency region of FIG. 13 with Image J, the actual region pitch 27.8 nm was measured. This means the pitch of the vertically oriented lamellar structure formed by the self-assembled structure of the polymer membrane formed inside the trench.

Comparative Example 1

The experiment was performed under the same conditions as in Example 1, except that the image of FIG. 1 was not subjected to the blurring processing and the integration of the Fourier-transformed image of FIG. 2 was performed. FIG. 7 shows the result of performing the radial integration in the range of 0° to 360° using image analysis software (US National Institute of Health [NIH] open source, "Image J") on the image of FIG. 2. As could be seen from FIG. 7, no peak was formed as a result of transforming the image without blurring processing. This is due to the noise generated because the trench structure formed on the substrate and the vertically oriented lamellar structure formed by the self-assembled structure of the block copolymer are aligned in the same direction, which shows the result that the pitch of the vertically oriented lamellar structure cannot be calculated.

Comparative Example 2

The experiment was performed under the same conditions as in Example 2, except that the image of FIG. 8 was not subjected to the blurring processing and the integration of the Fourier-transformed image of FIG. 9 was performed. FIG. 14 shows the result of performing the radial integration in the range of 0° to 360° using image analysis software (US National Institute of Health [NIH] open source, "Image J") on the image of FIG. 9. As could be seen from FIG. 14, no peak was formed as a result of transforming the image without blurring processing. This is due to the noise generated because the trench structure formed on the substrate and the vertically oriented lamellar structure formed by the self-assembled structure of the block copolymer are aligned in the same direction, which shows the result that the pitch of the vertically oriented lamellar structure cannot be calculated.

The invention claimed is:

1. A method for analyzing a polymer membrane comprising
blurring an original image of a polymer membrane having a block copolymer which is formed in trenches disposed at regular intervals and self-assembled to produce a blurring-processed image;
Fourier-transforming the original image and the blurring-processed image to produce a Fourier transformation result of the original image and a Fourier transformation result of the blurring-processed image;
removing noise from the Fourier transformation result of the original image and the Fourier transformation of the blurring-processed image;
wherein the removing noise includes removing an overlapping range of the Fourier transformation result of the original image and the Fourier transformation result of the blurring-processed image.

2. The method for analyzing a polymer membrane according to claim 1, further comprising:
measuring a pitch of a pattern formed on a surface of the polymer membrane from the Fourier-transformed result of the noise-removed original image.

3. The method for analyzing a polymer membrane according to claim 2, wherein the measuring the pitch includes measuring a peak formed by radially integrating the Fourier-transformed result of the noise-removed original image of the polymer membrane in the range of 0° to 360°.

4. The method for analyzing a polymer membrane according to claim 1, wherein the self-assembled structure of the block copolymer is a cylinder, sphere or lamellar structure.

5. The method for analyzing a polymer membrane according to claim 1, wherein the original image of the polymer membrane is an image obtained through a scanning electron microscope (SEM), an atomic force microscope (AFM) or a transmission electron microscope (TEM).

* * * * *